(12) United States Patent
Tawfiq et al.

(10) Patent No.: US 7,187,784 B2
(45) Date of Patent: Mar. 6, 2007

(54) BORESCOPE FOR DRILLED SHAFT INSPECTION

(75) Inventors: Kamal Tawfiq, Tallahassee, FL (US); Edward J. Mallory, Tallahassee, FL (US); Sastry Putcha, Tallahassee, FL (US); Dan Turner, Lake City, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 421 days.

(21) Appl. No.: 10/776,817

(22) Filed: Feb. 11, 2004

(65) Prior Publication Data

US 2004/0160514 A1 Aug. 19, 2004

Related U.S. Application Data

(63) Continuation-in-part of application No. 09/409,450, filed on Sep. 30, 1999, now abandoned.

(60) Provisional application No. 60/102,408, filed on Sep. 30, 1998.

(51) Int. Cl.
G06K 9/00 (2006.01)
G01V 1/40 (2006.01)
G01V 3/18 (2006.01)
E21B 47/00 (2006.01)
A61B 1/04 (2006.01)

(52) U.S. Cl. ........................ 382/109; 702/6; 73/152.02; 166/250.01; 175/50; 348/85

(58) Field of Classification Search ............... None
See application file for complete search history.

(56) References Cited

U.S. PATENT DOCUMENTS

| | | | |
|---|---|---|---|
| 4,079,625 A | 3/1978 | Mann | |
| 4,938,060 A | 7/1990 | Sizer et al. | |
| 5,123,492 A | 6/1992 | Lizanic, Jr. | |
| 5,255,245 A | 10/1993 | Clot | |
| 5,355,128 A | 10/1994 | Riordan | |
| 5,379,216 A * | 1/1995 | Head ........................... | 702/12 |
| 5,485,745 A | 1/1996 | Rademaker et al. | |
| 5,550,331 A | 8/1996 | Thompson | |
| 5,587,525 A * | 12/1996 | Shwe et al. ............... | 73/152.52 |
| 5,663,559 A | 9/1997 | Auzerais et al. | |
| 5,754,220 A | 5/1998 | Smalser, Sr. | |
| 5,996,711 A * | 12/1999 | Ohmer ........................ | 175/61 |
| 6,041,860 A | 3/2000 | Nazzal et al. | |
| 6,157,893 A * | 12/2000 | Berger et al. .................. | 702/9 |
| 6,164,126 A * | 12/2000 | Ciglenec et al. ......... | 73/152.01 |
| 6,281,489 B1 * | 8/2001 | Tubel et al. ........... | 250/227.14 |
| 6,307,199 B1 * | 10/2001 | Edwards et al. ......... | 250/269.3 |

* cited by examiner

Primary Examiner—Jingge Wu
Assistant Examiner—Charles Kim
(74) Attorney, Agent, or Firm—Senniger Powers

(57) ABSTRACT

Visual inspection of an interior surface of a borehole. A housing adapted to be lowered in the borehole supports a portable camera for generating images of a portion of the interior surface of the borehole and a light source for illuminating an area adjacent the camera. A monitor receives signals from the camera and, in response thereto, displays the images generated by the camera. A viewing envelope positioned adjacent the camera defines a viewing area adjacent the camera, particularly for use in visually inspecting slurry-filled boreholes.

31 Claims, 9 Drawing Sheets

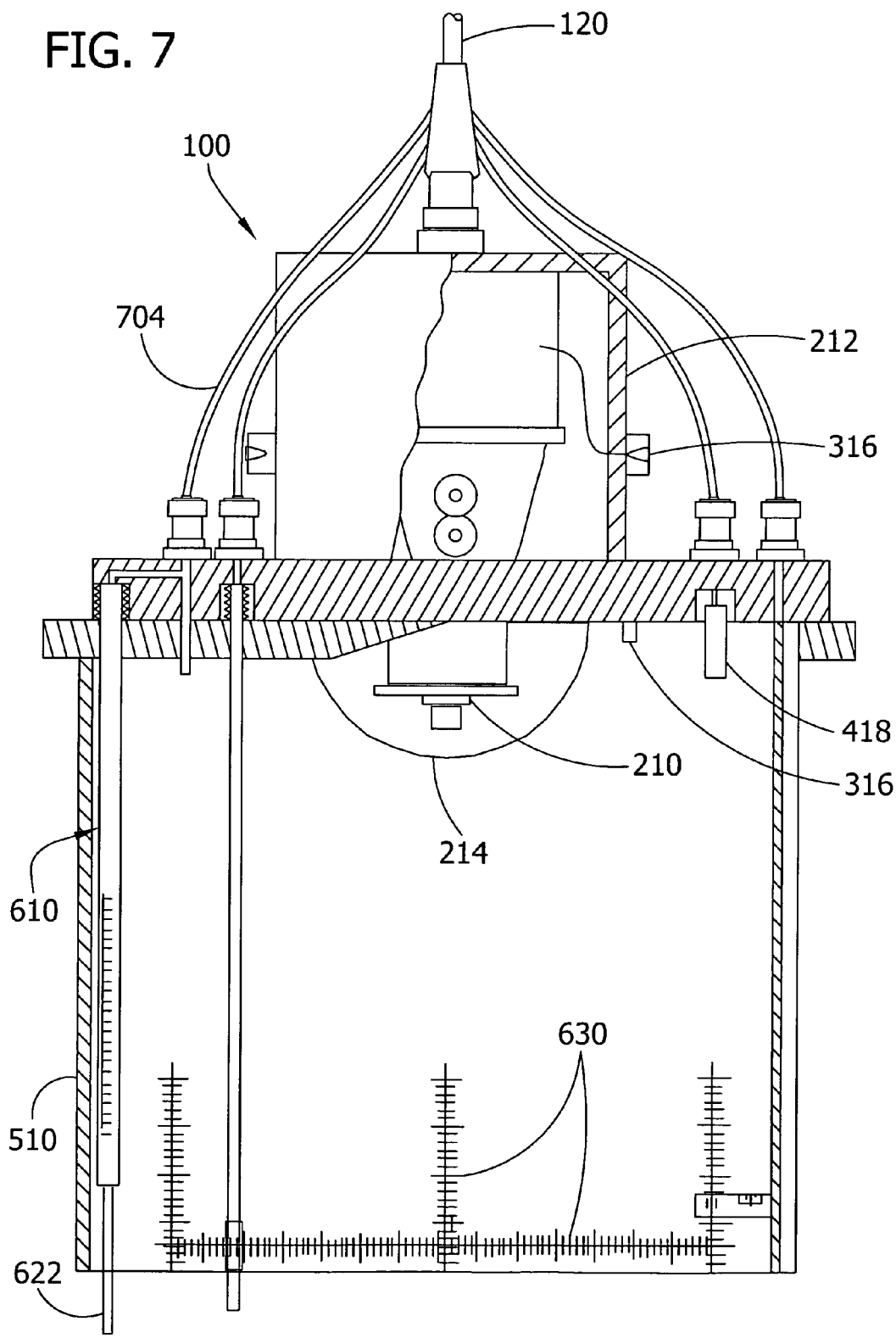

BORESCOPE FOR DRILLED SHAFT INSPECTION

CROSS REFERENCE TO RELATED APPLICATION

This application is a continuation-in-part of application Ser. No. 09/409,450, filed Sep. 30, 1999 now abandoned, which claims the benefit of provisional application Ser. No. 60/102,408, filed Sep. 30, 1998, the entire disclosures of which are incorporated herein by reference.

BACKGROUND OF THE INVENTION

The invention relates generally to a borescope system for use in inspecting drilled shafts, also referred to as bores or boreholes. In particular, the invention relates to a portable visual inspection system for inspecting relatively large drilled construction shafts and the like that provides improved efficiency in terms of maneuverability, information gathering, data recording, data analyzing, and data quantifying.

Drilled construction shafts that are subsequently filled with concrete or similar materials provide support for many large building projects. For this reason, field engineers and inspectors involved in preparing such shafts are particularly concerned with ensuring that the load transfers in side resistance and in end bearing are consistent with any assumptions made during the design phase. Normally, project design methods assume that drilled shafts are constructed under competent supervision and with ample quality control and assume that the finished foundation will be durable and have structural integrity. However, such assumptions are not always warranted. Unless project specifications and procedures are closely followed in the field, for example, the final shaft may have defects that can influence its structural and bearing capacity when filled. Therefore, the inspection of drilled shafts and the record keeping associated with shaft construction are important and require careful attention.

Defects of a finished support structure and the conditions under which such defects occur may involve a number of causes. For example, defects typically result from one or more of the following: 1) over stressing the soil beneath the shaft base due to insufficient bearing (contact) area or because of unconsolidated materials located at the shaft base; 2) excessive mixing from mineral slurry, which can affect the development of concrete strength and/or formation of voids and cavities within the set concrete; and 3) structural discontinuities and/or deviations from the true vertical line causing local, undesirable stress concentrations. In general, these and other defects can result in insufficient load transfer reducing the bearing capacity of the final structure and/or causing excessive settling during service.

To develop the required end bearing capacity, the drilled shaft should be inspected so that undesirable debris may be removed before concrete placement. Shaft failures have been attributed to insufficient borehole cleaning, and cleaning the base of boreholes often requires special tools. Although the operation sounds simple, a typical cleaning process involves several steps including visually inspecting the borehole, sounding the base of the shaft by a weight attached to a chain, and obtaining samples of the side walls and the base. Based on the results of the visual, sounding, and sampling inspections, a trained inspector decides whether the borehole must be cleaned or otherwise altered before concrete placement. The inspector usually bases his or her decision on the condition of the borehole and the amount of sedimentary deposits at the base. If the inspector decides that cleaning is warranted, several methods may be used, including air lifting, using a clean-out-bucket, or removing debris and unwanted material with a submerged pump. The cleaning requirements can be quite strict. For example, the Florida Department of Transportation requires that at least 50 percent of the base of each shaft have less than 0.5 inches (13 mm) of sediment at the time of concrete placement, and that the maximum depth of sedimentary deposits or any other debris at any place on the base of the shaft not exceed 1.5 inches (40 mm).

As may be expected, verifying the conditions existing at the shaft base is often a difficult task. Lowering a human inspector into a borehole, especially one that has been stabilized with slurry, can be very dangerous or even impossible. Thus, to facilitate the inspection process and to avoid sending human inspectors into large construction boreholes, highway agency guidelines often recommend the use of a shaft inspection device. The Florida Department of Transportation, for example, recommends the use of its Shaft Inspection Device (SID), developed in the early 1980s by Schmertmann and Crapps, Inc. The SID comprises a television camera sealed inside a water-tight jacket and is used for inspecting both dry and wet excavations. The concept of the SID was derived from an Australian drilled shaft inspection device originally developed by Dr. Jim Holden of the Country Roads Board.

Since its inception, the SID has been used with only modest success. The SID weighs approximately 10,000 pounds, is quite large, and is relatively expensive. Although the idea of utilizing an optical device to inspect drilled shafts has been favored by engineers and contractors, the operation of present devices like the SID is cumbersome, time consuming, expensive, and often produces disappointing results, especially on drilled shaft projects in waterways. In addition to the high cost of the device itself, the SID's lack of mobility and versatility, particularly in waterways projects, results in higher operating costs.

For these reasons, a portable visual inspection system for drilled shaft inspection with improved efficiency in terms of portability, information gathering, data recording, and quantifying the obtained measurements is desired. Such a system benefits from advancements in many technologies, including imaging, fiber optics, and computers and signal processing, as well as from the development of various types of miniature video scopes and borescope devices.

SUMMARY OF THE INVENTION

Embodiments of the invention overcome one or more deficiencies in the prior art by providing, among other things, an improved system for reliably and accurately visually inspecting relatively large construction boreholes such as those prepared for building drilled shaft foundations. The invention advantageously provides a visual inspection of the adequacy of boreholes (e.g., their bottom and sides) to construct deep foundations or slurry walls. Embodiments of the invention also determine the strength of the materials at the bottom of the boreholes as well as the physical and electrical properties, the pressure, and the temperature of the slurry in the borehole. This is accomplished by a portable system utilizing a miniature charge coupled device (CCD) camera in a watertight assembly and a miniature penetrometer The system of the present invention provides a smaller and lighter device for drilled shaft inspection that a single user can operate. Further, the invention does not require a complicated assembly but can be assembled on-site just prior to use. In one embodiment, an improved inspection system of the invention collects data in analog and/or digital form and is capable of providing digital information to a computer. Thus, it is economical in terms of the number of required personnel and efficient in storing and retrieving the needed information. Advantageously, the present invention is particularly well-suited for inspection in waterways projects and even provides clear vision in environments where visibility is limited. Moreover, the features of the present invention described herein are less laborious and easier to implement than currently available techniques as well as being economically feasible and commercially practical.

Briefly described, a system for inspecting a borehole embodying aspects of the invention includes a portable camera in a housing adapted to be lowered into the borehole. The camera, which has a defined viewing area, generates images of at least a portion of an interior surface of the borehole and generates signals representative of the generated images. The system also includes a sensor for use with the housing for sensing a physical characteristic of the borehole and a computer receiving and responsive to the signals from the camera and the sensed physical characteristic for inspecting the borehole.

Another embodiment of the invention involves a method of inspecting a borehole that contains a slurry. The method includes lowering a camera assembly into the slurry and determining a velocity at which the camera assembly is lowered. The method also includes measuring a buoyant weight of the camera assembly in the slurry and determining a density of the slurry as a function of a comparison between the measured buoyant weight of the camera assembly in the slurry and a reference weight of the camera assembly in air.

Another embodiment of a system for visually inspecting an interior surface of a construction borehole according to the invention includes a camera assembly, a load cell, and a computer. The camera assembly in this embodiment includes a portable camera for generating images of the interior of the borehole and for generating signals representative of the generated images. A housing provides the camera with viewing access and is adapted to be lowered into the borehole. The camera assembly also includes a viewing envelope positioned adjacent the camera and external to the housing. The viewing envelope has a transparent shell defining a fluid chamber and defining a viewing area adjacent the camera. A light source illuminates the viewing area, which enables the images of an interior surface of the borehole to be generated by the camera. Also, the viewing envelope has width substantially less than a width of the construction borehole. The load cell measures a buoyant weight of the camera assembly in a slurry relative to a reference weight of the camera assembly in air and the computer determines a density of the slurry in the borehole from the measured buoyant weight.

Yet another embodiment of the present invention relates to a system for visually inspecting a construction borehole. The system includes a portable camera for generating images of a portion of an interior surface of the borehole and a light source for illuminating a viewing area adjacent the camera. The light source enables the images of the interior surface of the borehole to be generated by the camera. The system also includes a housing for the camera and the light source that is adapted to be lowered into the bore hole. A probe for use with the housing measures a penetration of the probe on a bottom of the borehole and, in turn, determines an amount of a deposit at the bottom of the borehole. At least one of the images generated by the camera displays the probe. Further, the system includes a monitor receiving and responsive to signals from the camera for displaying the images generated by the camera.

Alternatively, the invention may comprise various other methods and systems.

Other objects and features will be in part apparent and in part pointed out hereinafter.

BRIEF DESCRIPTION OF THE DRAWINGS

FIG. 7 is a schematic view of the camera assembly of FIG. 1 including the observation chamber of FIG. 5.

Corresponding reference characters indicate corresponding parts throughout the drawings.

DETAILED DESCRIPTION OF THE INVENTION

Figure 1:
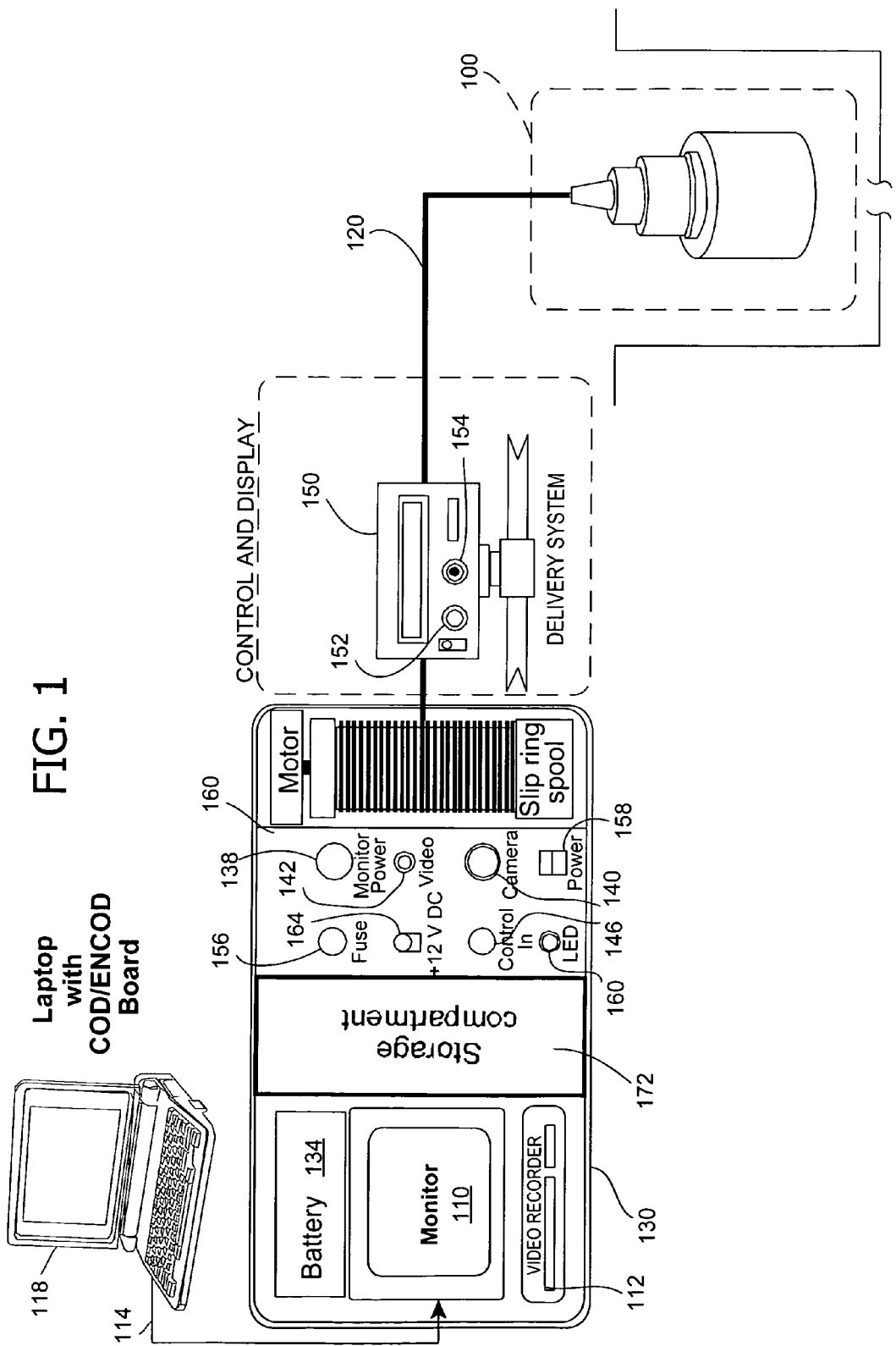
FIG. 1 is a block diagram of a borescope system for visually inspecting drilled shafts according to an embodiment of the invention.

Referring now to the drawings, FIG. 1 illustrates a borescope system in block diagram form. As shown, the system includes a camera assembly 100 connected to a video monitor 110 (e.g., a relatively small, portable television) for visually inspecting a borehole. A typical borehole is several feet in diameter (e.g., about nine feet) and has an even greater depth (e.g., about 150 feet). It is to be understood, however, that a borehole describes any opening in the ground that has either a generally cylindrical geometry of a few inches to several feet in diameter and depth or a generally rectangular cutoff wall in the ground with a few inches to several feet in width/depth. The borehole can be dry or wet (at least partially filled with transparent, translucent, or opaque fluid). The borehole can be self supported, cased, or a pipe pile. The ratio of the size of the borehole to the camera chamber can be 1:1 or 28:1.

As described in detail below, the present system may be used to visually inspect the adequacy of boreholes (bottom and sides) to construct deep foundations or slurry walls. In addition, the system is able to determine the strength of the materials at the bottom of the boreholes by using a miniature penetrometer; and to determine the physical and electrical properties, the pressure, and the temperature of the slurry in the borehole.

According to embodiments of the invention, the camera assembly 100 generates images of the shaft's interior surfaces while suspended in the borehole. As illustrated, the video monitor 110 has a video recorder 112 (e.g., a video cassette recorder, digital video recorder or other recording system) for recording the video images captured by camera assembly 100 in analog form or digital form depending on the video format. In one embodiment, the borescope system also provides a line 114 to a computer 118 for displaying and recording the captured images. In the embodiment shown, camera assembly 100 communicates with the computer 118 via a power-video-control cable 120 (also referred to as an umbilical cord). Camera assembly 100 communicates with computer 118 according to, for example, an RS232 standard. It is to be understood that computer 118 may be used in addition to or instead of the video monitor 110 and recorder 112 for recording the video images of the interior of the borehole generated by camera assembly 100.

The borescope system of the invention also has a case 130 for housing, storing, and transporting various components of the system. Advantageously, the case 130 houses a rechargeable battery 134 for supplying power to the various components of the system. An appropriately wired connector panel 136 known to those skilled in the art provides easy electrical connections between the various components such as the battery 134, camera assembly 100, video monitor 110, and/or computer 118.

Although computer 118 is shown as a laptop computer in FIG. 1, other computer configurations are easily adapted for use with the present invention. Moreover, computer 118 may be self-powered (e.g., independently battery powered), receive power from battery 134, or receive power from an external source independent of the borescope system.

In the illustrated embodiment, battery 134 supplies power to video monitor 110 and recorder 112 via a monitor power connection 138 and a power line (not shown). Battery 134 also supplies power to camera assembly 100 via a camera input 140 and the power-video-control cable 120. In the embodiment shown in FIG. 1, the line 114 supplies a video signal to computer 118 (or another external monitor) via a video connector 142. The connector panel 136 also includes a control input 146 described below.

As will be explained in greater detail below, a controller 150 controls camera assembly 100. The controller 150 is connected on one side, by the umbilical cord containing power-video-control cable 120 to computer 118. Controller 150 is connected on another side to the control input 146 on connector panel 136. As shown in FIG. 1, controller 150 further includes a pan controller 152 and a tilt controller 154. Borescope system operators can manipulate the camera's position using the controllers 152 and 154. Control signals generated by controllers 152,154 are transmitted to camera assembly 100 via power-video-control cable 120. Additionally, the RS232 link between computer 118 and camera assembly 100 is established via controller 150. Thus, it is possible to generate and transmit computer controlled input information to camera assembly 100 via controller 150. Likewise, computer 118 can receive camera information, such as camera position information, from camera assembly 100 via controller 150.

The connector panel 136 also provides access to a power supply fuse 156, as well as a system power switch 158 and a power indicator 160. Although it is anticipated that the borescope system will often operate using the battery 134, the system may also be connected directly to an external power source using a power line (not shown) connected via a power connector 164. The external power line and power connector 164 may also be used to recharge the battery 134 when the system is not being used. Although the embodiment shown in FIG. 1 contemplates the use of a 12 volt power system, the borescope system of the present invention is in no way limited to 12 volt systems. Additionally, the case 130 also includes at least one storage compartment 172 for storing various components of the borescope system when the system is not in use or being transported.

Advantageously, a borescope system according to the invention permits control, measurement, and/or display of camera assembly depth, buoyant weight, and/or descending velocity as well as electrical conductivity, pressure, and/or temperature of the slurry contained in the borehole.

Figure 2:
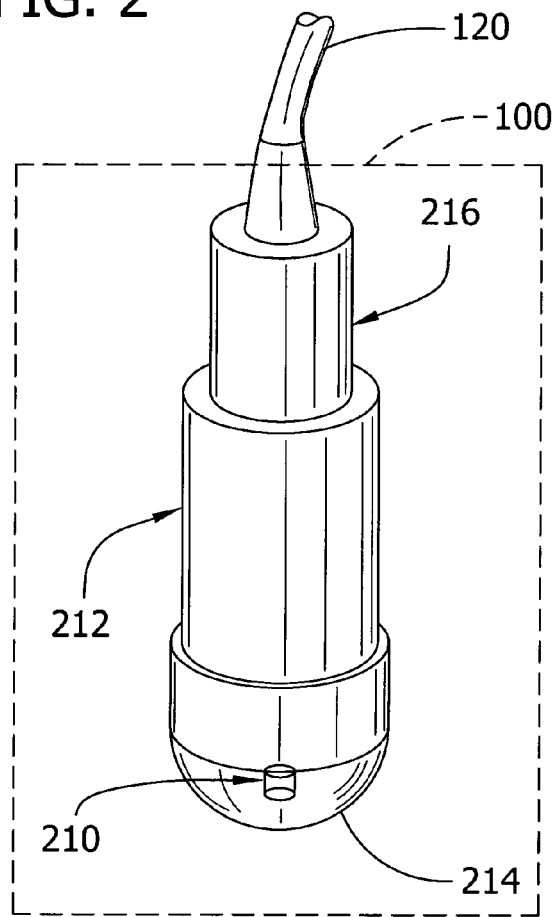
FIG. 2 is a view of a camera assembly of the system of FIG. 1.

Referring now to FIG. 2, camera assembly 100 includes a miniature (e.g., about the size of a highlighter pen) color or black and white charge coupled device (CCD) video camera 210. In one embodiment, the width of camera assembly 100, including the miniature camera 210, is substantially less than the diameter of the borehole under inspection.

Figure 4:
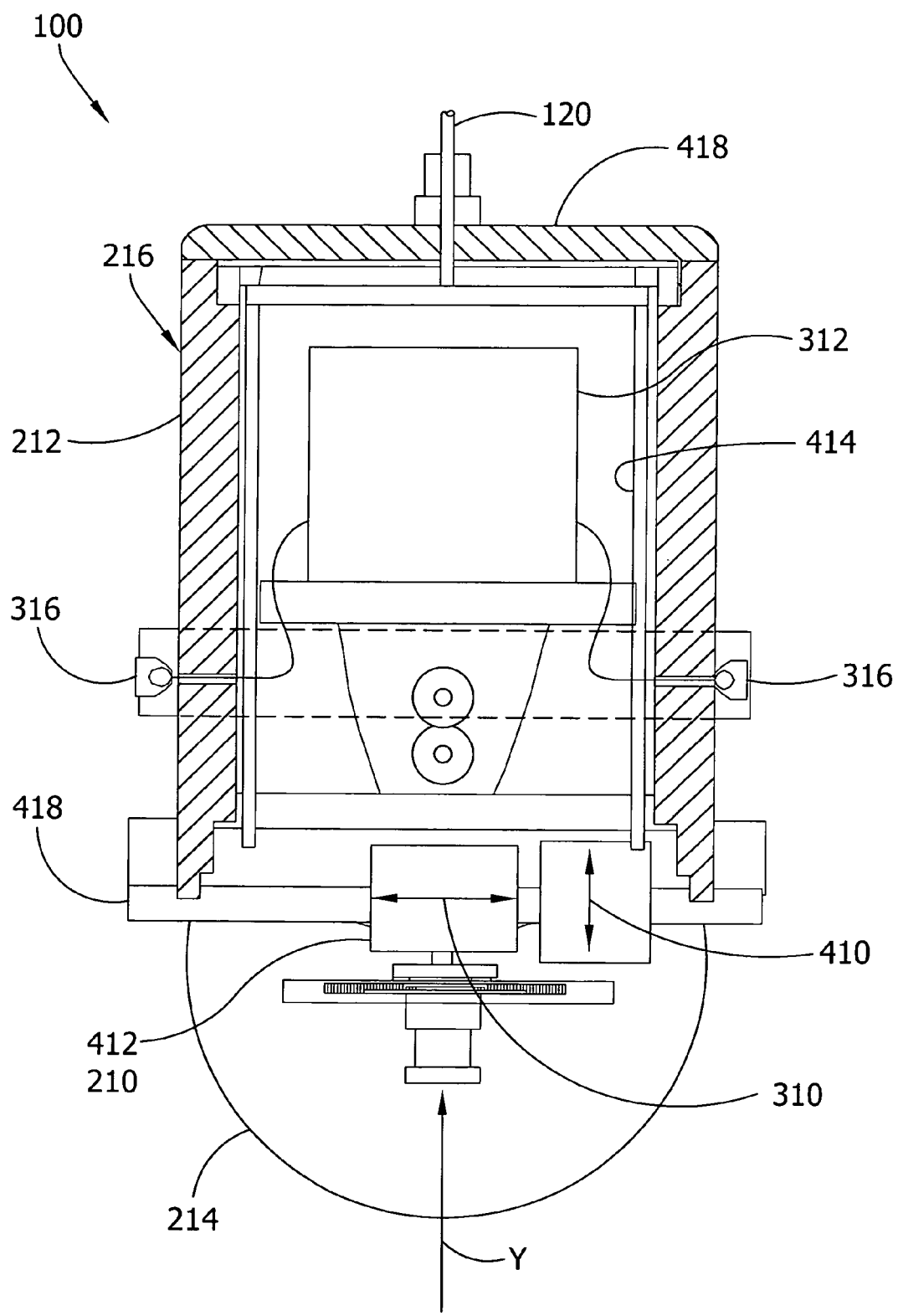
FIG. 4 is a schematic view of the camera assembly of FIG. 1.

The camera 210 may be housed within a housing chamber 212 for protection. This camera assembly housing chamber 212, generally cylindrical in this embodiment, is constructed using a rigid material such as aluminum. It is to be understood, however, that other materials, such as PVC, may be suitable for protecting camera 210. In fact, as shown in FIG. 4 below, one embodiment of the housing chamber 212 of the present invention uses an aluminum frame enclosed in a PVC casing. An abrasion resistant transparent dome 214 provides camera 210 with viewing access while protecting the camera 210 from possible damage due to contact with the surfaces being inspected. Although the transparent dome 214 in the embodiment illustrated in FIG. 2 is constructed of plastic, any number of transparent materials could be used with the borescope system of the present invention. Power-video-control cable 120 is connected to the end of camera assembly 100 at a rear closure 216. The rear closure 216, in turn, connects to housing chamber 212. Housing chamber 212, rear closure 216, and transparent dome 214 are assembled using methods known in the art to create a substantially watertight protective housing for the camera assembly 100.

Figure 3:
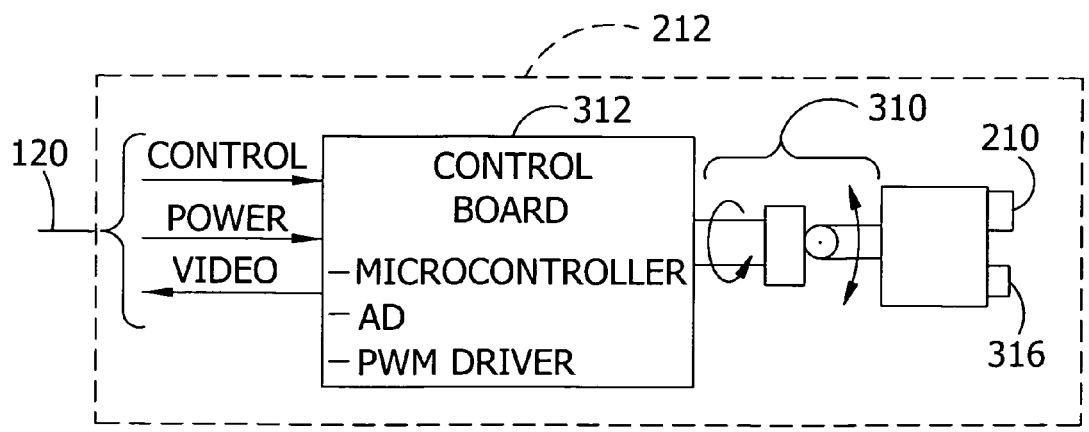
FIG. 3 is a view of a tilt and pan gear and of a light source of the camera assembly of FIG. 1.

Referring now to FIG. 3, the housing chamber 212 of camera assembly 100 also encloses a tilt and pan gear mechanism 310, on which camera 210 is mounted. A system operator controls the tilt and pan gear mechanism 310 to rotate camera 210 through a wide range of motion leg (e.g., 360 degrees in-plane and 180 degrees out-of-plane). Camera rotation is explained in further detail below.

In addition to camera 210 and tilt and pan gear mechanism 310, the housing chamber 212 also encloses an electronic control board 312 and one or more high intensity light emitting diodes 316. Preferably, the light emitting diodes 316 provide sufficient illumination to enable camera 210 to capture images of the interior of the borehole under inspection. The control board 312 controls camera 210 and tilt and pan gear mechanism 310 in response to operator inputs from controller 150 via power unit 132 and power-video-control cable 120 (see also FIG. 1). By manipulating tilt and pan gear mechanism 310, also referred to as a motion control mechanism, the operator can control and direct a camera viewing angle or line of sight, which in turn enables the operator specify areas of the borehole for viewing and inspection.

FIG. 4 is a schematic illustrating certain detailed aspects of the camera assembly 100 of a borescope system according to the present invention. As shown in FIG. 4, the camera assembly housing chamber 212 supports tilt and pan gear mechanism 310 which includes a vertical servo motor 410 for tilting camera 210 and a horizontal servo motor 412 for rotating it. The functionality of tilt and pan gear mechanism 310 may be further described by reference to the vertical servo motor 410 and the horizontal servo motor 412. The tilt mechanism and vertical servo motor 410 constitute a first rotational motion stage for rotating camera 210 in a plane defined by a vertical axis y relative to the housing chamber 212, i.e., tilting camera 210 up to approximately 180 degrees (±90 degrees), as camera 210 is suspended in the borehole. Likewise, the pan mechanism and horizontal servo motor 412 constitute a second rotational motion stage for rotating camera 210 about the vertical axis y over approximately 360 degrees as camera 210 is suspended in the borehole.

Referring to both FIG. 3 and FIG. 4, control board 312 provides servo motors 410, 412 with electrical control signals in response to operator inputs from the tilt and pan controllers 152,154 of controller 150 (see FIG. 1). In particular, control board 312 includes a micro-controller with an analog-to-digital (A/D) converter and a pulse width modulation output driver. The micro-controller receives analog input signals from tilt and pan controllers 152, 154 and converts the received signals to pulse width modulated output signals for accurately controlling the position of servo motors 410, 412 using control and driver techniques that are known in the art.

FIG. 4 further illustrates housing chamber 212 previously described with respect to FIG. 2. As shown in FIG. 4, housing chamber 212 is comprised of a generally cylindrical aluminum frame 414 enclosed in a generally cylindrical PVC casing 416. Generally disk-shaped PVC end caps 418 are used to enclose each end of housing chamber 212.

In an alternative embodiment, aluminum stands (not shown) support camera assembly 100 on the bottom of the borehole to be inspected. Aluminum brackets (not shown) may be attached to the PVC casing 416 to provide additional support for housing chamber 212 and for receiving and supporting the aluminum stands.

Figure 5:
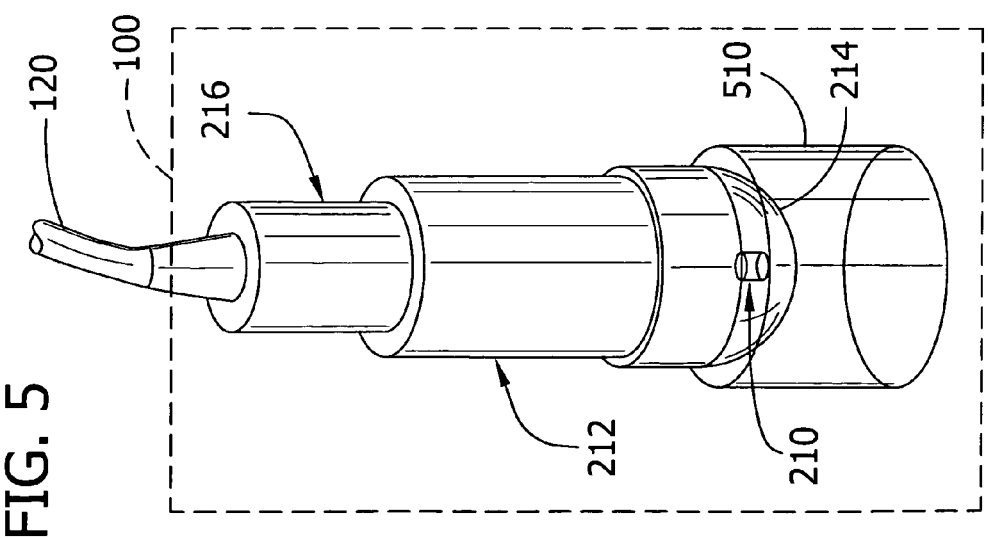
FIG. 5 is a view of an observation chamber for use with the camera assembly of FIG. 1.

In another embodiment, the borescope system employs a fluid-filled viewing envelope 510 as shown in FIG. 5 connected to housing 212. The viewing envelope 510, also referred to as an observation chamber, is particularly well-suited for use in slurry-filled boreholes. As is known in the art, boreholes are often filled with a viscous mud, or slurry, especially in waterways projects. The slurry, however, obscures the view of the side walls and bottom of the filled borehole. According to the invention, the viewing envelope 510 is attached to the camera assembly 100 and filled with a clear liquid such as water. The camera 210 is separated from the fluid by the transparent dome 214.

Fluid describes materials of gas or liquid nature. A fluid chamber (i.e., viewing envelope 510) can be used to inspect the verticality of a borehole and quantitatively determine the angle of tilt of the borehole (using a horizontal air bubble or a laser beam attached to the fluid chamber). The viewing envelope 510 consists of either a rigid or a flexible transparent material. Moreover, viewing envelope 510 is either closed end or open end. For example, in a dry borehole, it may be desired to detach the chamber from the camera assembly and the inspection can be carried out with camera assembly 100 alone.

The present invention may be used to determine the adequacy of the boreholes. Cleanliness of the bottom and sides of the borehole from any soil or rock residues is an important factor for determining whether the borehole is adequate for constructing deep foundations or slurry walls. Also, the concept of borehole adequacy describes cracking in pipe piles or defects in borehole casing.

Advantageously, the fluid in viewing envelope 510 provides camera 210 with a viewing interface. In operation, the operator lowers camera assembly 100, with viewing envelope 510 attached, into a slurry-filled borehole. By moving the assembly 100, particularly the viewing envelope 510, into contact with the side walls or bottom of the borehole, the operator is able to obtain images of the borehole's interior surface even though the assembly 100 is submerged in the slurry. In this manner, viewing envelope 510 defines a viewing area of the camera 210 in situations where a camera could not otherwise view the walls or bottom of the borehole.

In addition to providing a clear viewing interface, the water in viewing envelope 510 counters the pressure of the slurry against its surface and adds weight to the overall assembly 100. This helps stabilize camera assembly 100 and is an improvement over an air-filled observation chamber. As illustrated in FIG. 5, viewing envelope 510 is a generally cylindrical structure constructed of rigid, transparent plastic or a similar material. In an alternative embodiment, viewing envelope 510 is made of a flexible, durable, transparent plastic. In this alternative embodiment, the water contained in the viewing envelope 510 sufficiently maintains the chamber's volume while the flexible plastic more uniformly conforms to the non-uniform interior surface of the borehole.

Figure 6:
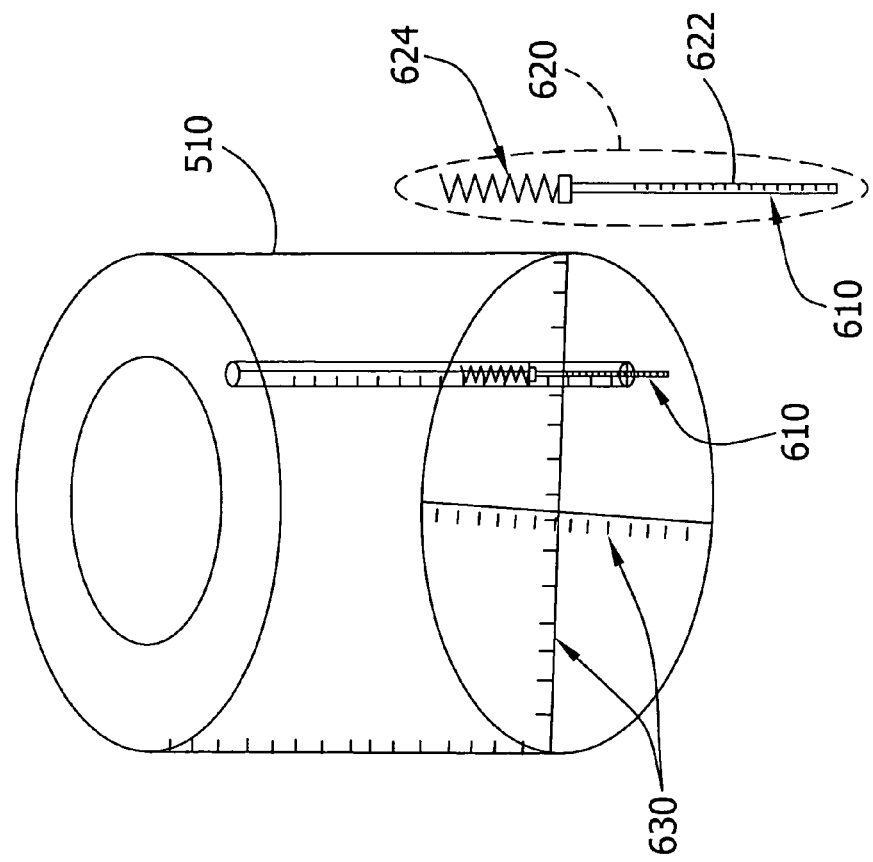
FIG. 6 is a view of a penetrometer for use with the observation chamber of FIG. 5.

FIG. 6 shows a penetrometer 610 for use with viewing envelope 510. In this embodiment, the penetrometer 610 measures the stiffness of the bottom of the borehole with, for example, a spring-loaded steel bar assembly 620 projecting therefrom having a graduated steel bar 622 connected to a spring 624. If the bottom of the borehole is relatively stiff, or solid, it will provide resistance and push up the steel bar 622 and likewise compress the spring 624. On the other hand, if the bottom of the borehole is soft, it will not provide as much resistance and, thus, will push the steel bar 622 and compress the spring 624 by lesser amounts. The penetrometer 610, which may be mounted on a surface of the viewing envelope 510, for example, is calibrated to measure stiffness as a function of the amount of deflection of the spring-loaded steel bar assembly 620. It should be understood, however, that penetrometer 610 could be employed separately, without viewing envelope 510.

FIG. 6 further shows a viewing envelope 510 that includes graduated scale markings 630. The graduated scale markings 630 would be captured by the video camera and could be used to take relative measurements. For example, the size of a shaft anomaly could be measured against graduated scale markings 630. In this instance, the invention identifies any debris existing at the bottom of the shaft and is able to measure the debris for acceptance using the vertical and horizontal graduated scale 630 of viewing envelope 510.

The penetrometer 610, along with viewing envelope 510, can be used to determine the thickness of the sediments and the unconfined strength of the materials at the bottom of the borehole. Penetrometer 610 can be mechanical with a calibrated spring or pneumatic.

FIG. 7 is a schematic view of the camera assembly of FIG. 1 including viewing envelope 510, and illustrating further details of the invention. In this embodiment of the present invention, viewing envelope 510 forms a graduated observation chamber marked with vertical and/or horizontal scaling. It is to be understood that viewing envelope 510 may be open-ended or closed-ended. If closed-ended, it may be desired to fill the observation chamber with water or another transparent liquid. In an alternative embodiment, an air line 704 supplies pressurized air to the observation chamber.

Figure 8:
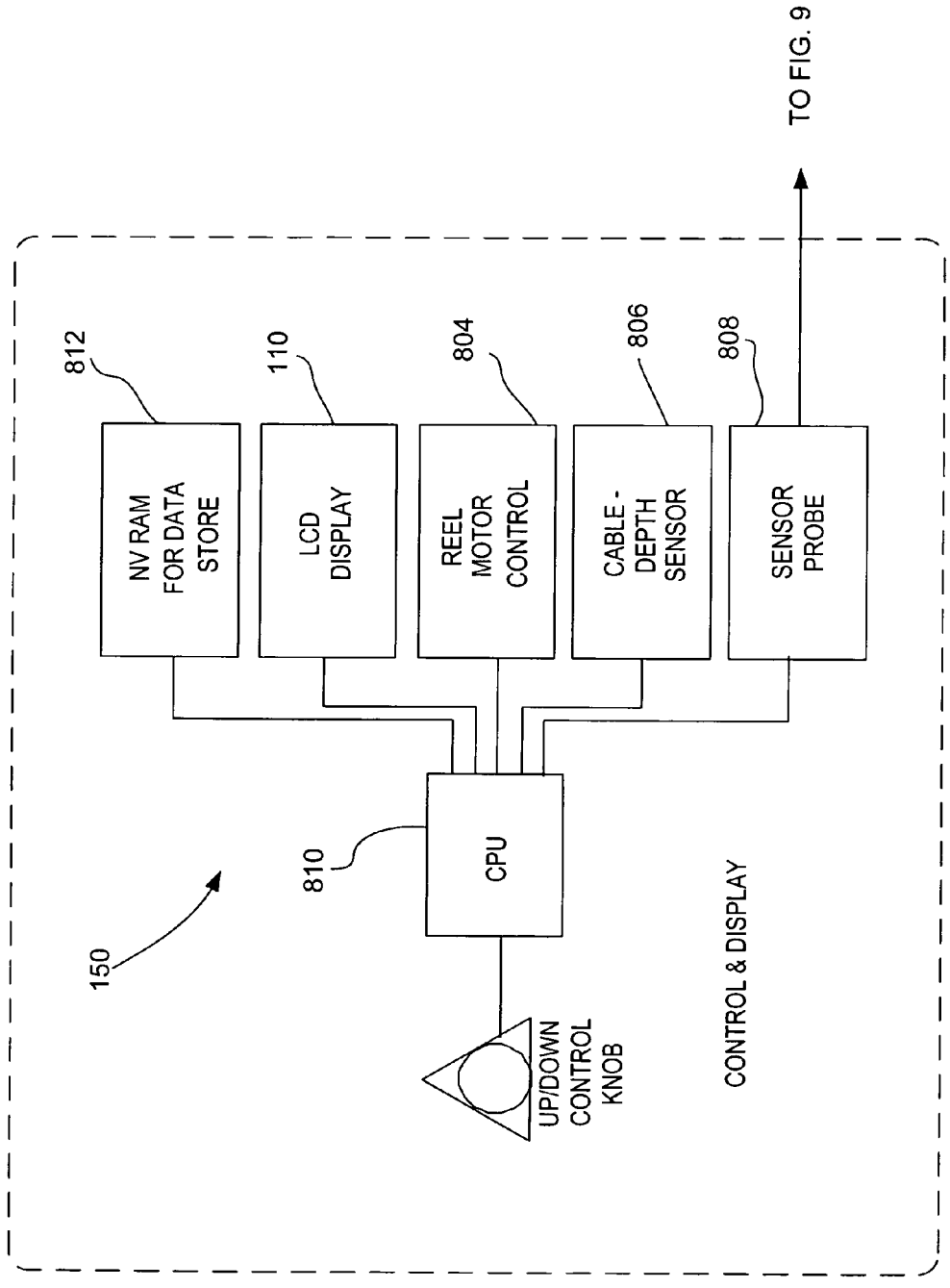
FIG. 8 is a block diagram of a borescope system for visually inspecting drilled shafts according to another embodiment of the invention.

Those skilled in the art will appreciate the importance of measuring several physical characteristics of the slurry. FIG. 8 illustrates further aspects of a borescope system according to the invention in which computer 118 cooperates with controller 150 and monitor 110 (e.g., a liquid crystal display panel). In operation, a reel motor control 806 is responsive to user input via controller 150 for raising or lowering camera assembly 100 within a borehole under inspection. A cable depth sensor 806 provides information regarding the depth of camera assembly 100 at any given instant as it drops into the drilled shaft. In addition, one or more sensor probes 808 (see FIG. 9) may provide information to central processing unit 810 regarding any of a number of characteristics of the borehole. A memory 812 associated with computer 118 stores the gathered information in this embodiment of the invention.

In other words, FIG. 8 shows the components of a control and display unit according to embodiments of the invention. For example, sensor probes 808 encompass sensors and measurements shown in FIG. 9, including load cell 902 (for unit weight and viscosity measurements) (see FIG. 10); thermocouple 904 (for temperature measurement); conductivity probe 906 (for electric conductivity measurement of the slurry) (see FIG. 11); and pressure gauge 908 (for slurry pressure measurement). Those skilled in the art are familiar with thermocouples and pressure gauges suitable for use with the invention.

Figure 9:
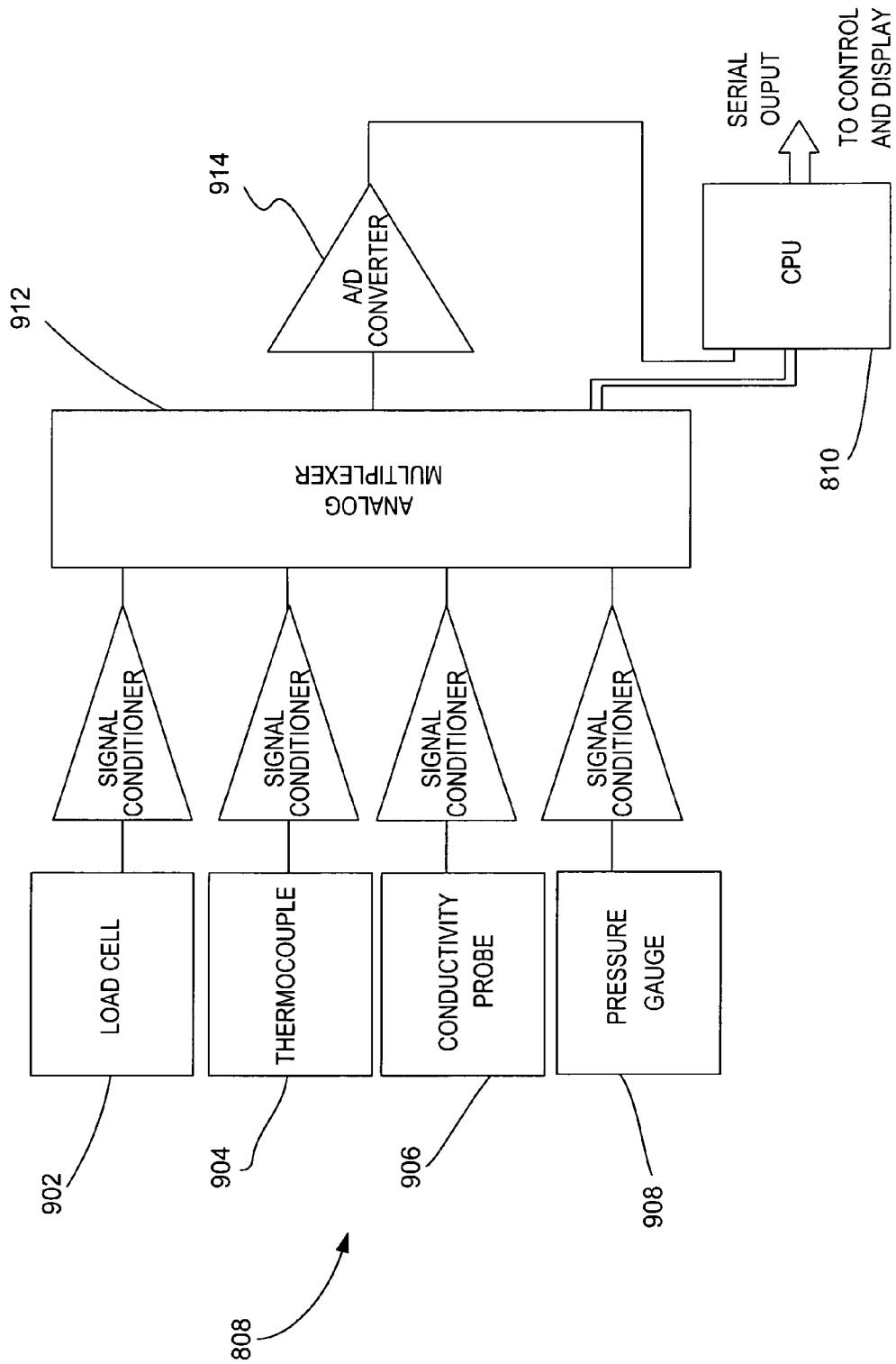
FIG. 9 is a block diagram of control circuitry for use with the borescope system of FIG. 8.

Referring now to FIG. 9, the sensor probe 808 may constitute one or more sensors including, but not limited to, a load cell 902, a thermocouple 904, a conductivity probe 906, and a pressure gauge 908. For example, the pressure gauge 908 measures pressure on camera assembly 100 as exerted by the slurry in the borehole and the thermocouple 904 measures temperature of the slurry. As shown, the control circuitry of FIG. 9 conditions the sensor signals and prepares them for processing by computer 118. For example, the analog sensor signals are conditioned and then multiplexed by an analog multiplexer 912 before being converted to digital signals by an analog/digital converter 914 for processing by computer 118. The load cell arrangement, including load cell 902, along with the reel motor control 804 and the cable depth sensor 806 are used to measure the unit weight, the viscosity of the slurry, and the depth at which the measurements are taken.

Figure 10:
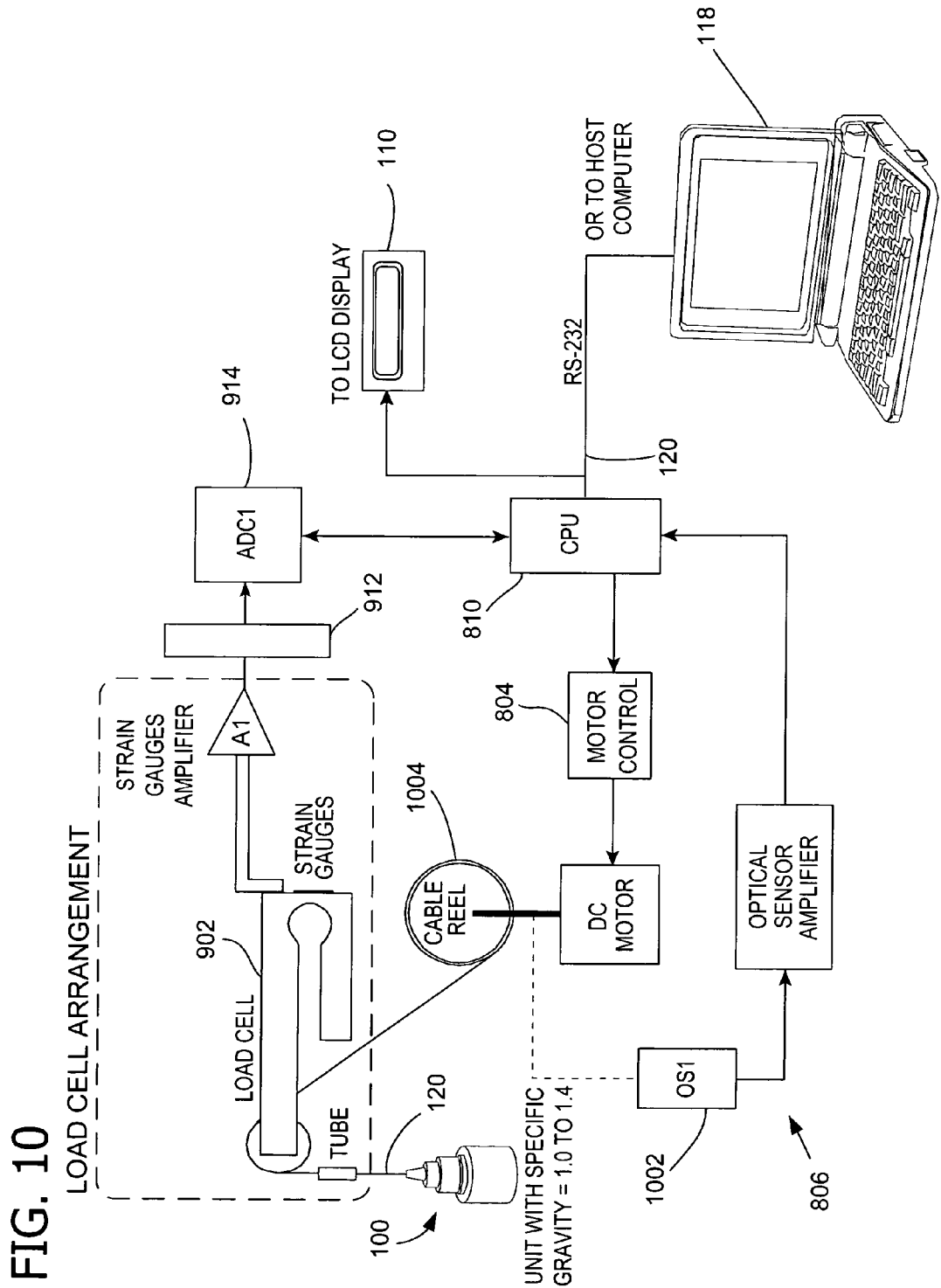
FIG. 10 is a block diagram of a load cell arrangement associated with the control circuitry of FIG. 9.

FIG. 10 shows an exemplary load cell arrangement including the load cell 902 of FIG. 9 for obtaining unit weight and viscosity measurements. Advantageously, the load cell arrangement permits determination of the unit weight and the viscosity of the slurry fluid, at different depths, as a function of the slurry's physical properties. For example, camera assembly 100 including the fluid chamber (i.e., viewing envelope 510) has a predetermined specific gravity that ranges from 1 to 1.4. Based on the anticipated density of the slurry fluid in the borehole, the camera chamber size 212 can be selected to get the desired specific gravity (1 to 1.4). This specific gravity of the borescope is very important to determine the unit weight and the viscosity of the slurry fluid in the borehole.

The camera assembly 100, including viewing envelope 510, can be lowered in the slurry fluid under a substantially constant velocity (i.e., a controlled fall). At different depth intervals, a control unit at the surface such as computer 118 detects its depth and buoyant weight from which the unit weight of the slurry can be determined. A digital readout unit at the surface displays the relationship between depths versus unit weight. In one embodiment, load cell 902, according to the arrangement of FIG. 10, determines the weight of camera assembly 100 and the cable depth sensor 806 determines its depth. For example, cable depth sensor 806 comprises an optical wheel sensor 1002 associated with a cable reel 1004 used for raising and lowering camera assembly 100 by its umbilical cord 120.

Figure 11:
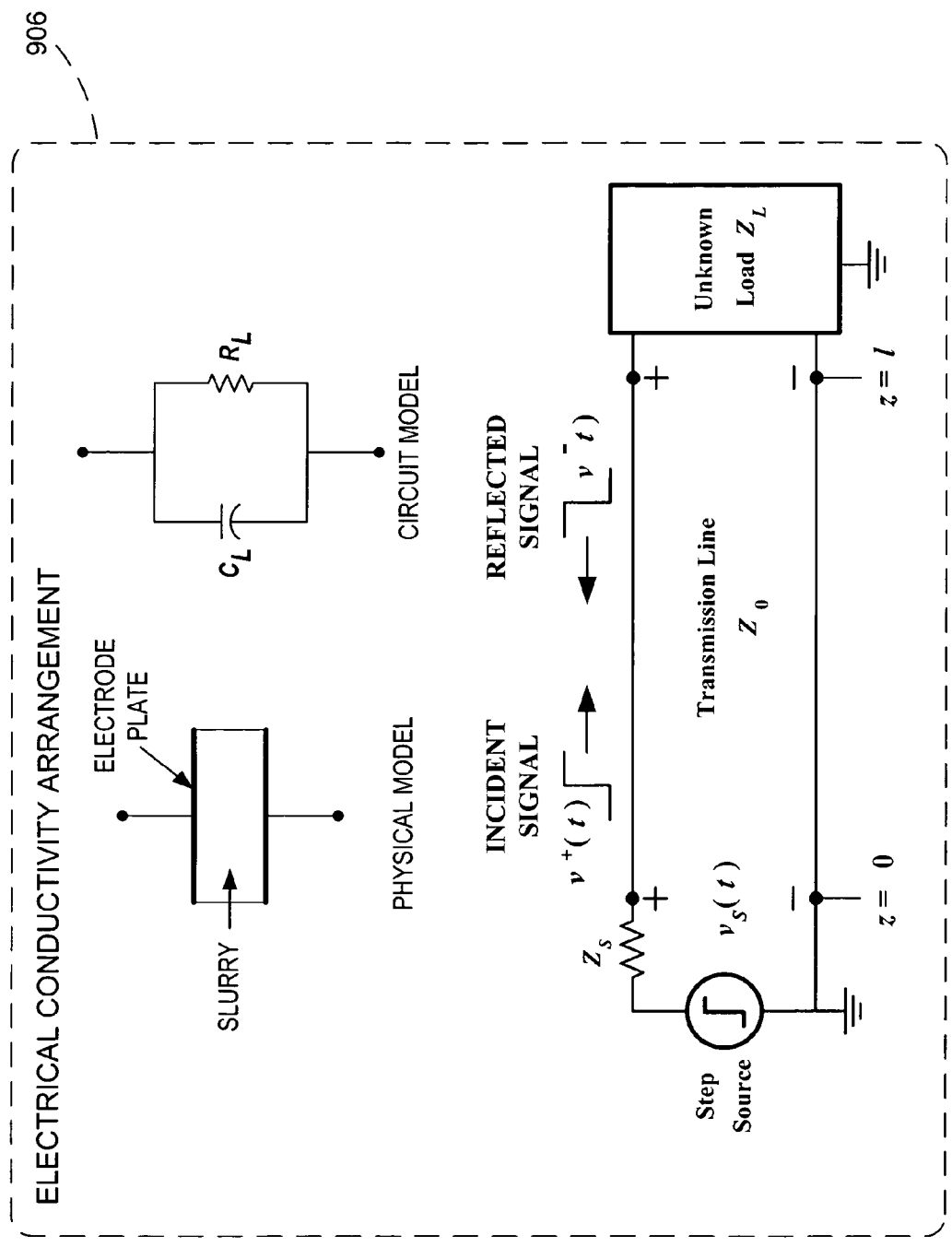
FIG. 11 is a block diagram of an electrical conductivity arrangement associated with the control circuitry of FIG. 9.

Referring now to FIG. 11, an exemplary electrical conductivity arrangement including the conductivity probe 906 is shown. Advantageously, the present invention determines at least one electrical property of the slurry such as its electrical conductivity. Conductivity probe 906 in one embodiment extends from viewing envelope 510 for measuring electrical conductivity of the slurry with the depth. Measurements of the electrical conductivity are displayed on the control unit.

In yet another embodiment, camera assembly 100 includes a soil sampler (not shown) for use with viewing envelope 510 in addition to or instead of the penetrometer 610.

The invention assists in determining the suitability of a drilled shaft borehole for pouring concrete without the need for sending an inspector or diver to inspect the bottom or sides of the hole. Additionally, data is stored on video recorder 112 and/or computer 118, or on similar recording devices. The stored data can be used on site or during subsequent analysis in assessing the load carrying capacity of drilled shafts.

Moreover, the borescope system of the present invention provides qualitative as well as quantitative measurements to assist in determining the amount of sedimentary deposits and contamination in the boreholes rather than relying on the personal judgment of the drilled shaft inspector. When the invention is employed using a computer with MPEG or similar capability, the analog video images may be converted to digital images that an inspector or analyst can manipulate using digital filters, for example, to extract information that may not be detectable from a visual inspection of the shaft surfaces. For example, each pixel in an image would be mapped and given a value based on its optical characteristics. An image processor would then process the pixel data. In an alternative embodiment, a digital video camera may be used that provides both a video image as well as digital information regarding the image. Digital filtering and image processing techniques suitable for use with the present invention are known in the art and need not be described further herein.

The invention also has the advantage of advanced maneuverability. The operator can maneuver the video camera at various angles allowing inspection of the side walls of the shaft. Conventional inspection devices cannot perform this function. Furthermore, these processes can be conducted and monitored in real time and records can be stored digitally and/or reproduced on hard copies for later analysis and final reporting. Also, the digitized images and data can be added to a data base on drilled shaft construction and used to improve existing design/construction methods. This device provides engineers with an alternative to the SID at a much lower cost and with higher efficiency and productivity.

In one embodiment, the system comprises a portable inspection unit that can be transported and operated by a single inspector. Reconfiguring the basic unit to accommodate additional inspection sensors is also contemplated. Such sensors include probes to obtain soil specimens for further inspection, probes to measure penetration resistance of the bottom soil, or ultrasound or similar penetrating sensors to gather information below surficial sediments.

These additions are regarded as accessories and may be added to the basic unit when field conditions require such accessories.

Advantageously, such a system provides both portability and versatility to facilitate the process of shaft inspection in a timely manner. Thus, one or two inspectors can perform the job with great efficiency and without causing delays in the construction stage of the drilled shafts. Furthermore, the borescope system of the present invention is not limited to vertical drilled shafts and may be used to inspect non-vertical shafts by adjusting or substituting the structure used to support and/or suspend the camera and housing into the shaft.

When introducing elements of the present invention or the embodiment(s) thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A method of inspecting a borehole containing a slurry, said method comprising:
   lowering a camera assembly into the slurry, said camera assembly having a reference weight in air;
   determining a velocity at which the camera assembly is lowered;
   measuring a buoyant weight of the camera assembly in the slurry;
   determining a density of the slurry as a function of a comparison between the measured buoyant weight of the camera assembly in the slurry and the reference weight of the camera assembly in air.

2. A system for visually inspecting an interior surface of a construction borehole containing a slurry, said system comprising:
   a camera assembly, said camera assembly comprising:
      a portable camera for generating images of a portion of the interior surface of the borehole and for generating signals representative of the generated images;
      a light source for illuminating an area adjacent the camera thereby enabling the images of the interior surface of the borehole to be generated by the camera;
      a housing for the camera and the light source, said housing providing the camera with viewing access and adapted to be lowered into the borehole;
      a viewing envelope positioned adjacent the camera and external to the housing, said viewing envelope comprising a transparent shell defining a fluid chamber and defining a viewing area adjacent the camera, said light source illuminating the viewing area, and said viewing envelope having a width less than a width of the construction borehole; and
      a load cell for measuring a buoyant weight of the camera assembly in the slurry relative to a reference weight of the camera assembly in air; and
      a computer receiving and responsive to the measured buoyant weight for determining a density of the slurry in the borehole.

3. The system of claim 2 further comprising a video recorder for recording the images generated by the camera.

4. The system of claim 2 farther comprising a monitor receiving and responsive to the signals from the camera for displaying the images generated by the camera.

5. The system of claim 2 farther comprising an image processor for acquiring an image of the interior surface of the borehole from the images generated by the camera and for processing the acquired image.

6. The system of claim 5 wherein the images generated by the camera each include a plurality of pixels, said pixels each having a value representative of an optical characteristic of the images, and wherein the image processor processes the acquired image of the interior surface of the borehole as a function of the pixel values.

7. The system of claim 2 further comprising a rechargeable power supply for supplying power to the camera and/or the monitor.

8. The system of claim 2 wherein the fluid chamber of the viewing envelope is filled with water.

9. The system of claim 2 wherein the transparent shell comprises a rigid plastic.

10. The system of claim 2 wherein the transparent shell comprises a flexible plastic.

11. The system of claim 2 further comprising a rotational motion stage for tilting the camera in a plane relative to an axis of the housing.

12. The system of claim 2 further comprising a rotational motion stage for rotating the camera about an axis of the housing.

13. The system of claim 2 further comprising a probe for use with the housing for measuring penetration on a bottom of the borehole and determining an amount of a deposit at the bottom of the borehole and wherein at least one of the images generated by the camera displays the probe.

14. The system of claim 13 wherein the probe comprises a graduated bar protruding from the housing and connected to the housing by a spring, said graduated bar being in the viewing area of the camera.

15. The system of claim 2 wherein the housing includes a transparent dome through which the camera has viewing access.

16. The system of claim 2 wherein an outer width of the housing is less than the width of the construction borehole.

17. The system of claim 2 wherein the fluid chamber of the viewing envelope is filled with air.

18. A system for visually inspecting an interior surface of a construction borehole, said system comprising:
   a portable camera for generating images of a portion of the interior surface of the borehole and for generating signals representative of the generated images, said camera defining a viewing area adjacent the camera in which the images are generated;
   a light source for illuminating at least a portion of the viewing area adjacent the camera thereby enabling the images of the interior surface of the borehole to be generated by the camera;
   a housing for the camera and the light source, said housing adapted to be lowered into the borehole;
   a probe for use with the housing for measuring a penetration resistance of the probe on a bottom of the borehole and determining an amount of a deposit at the bottom of the borehole as a function of the measured penetration resistance and wherein at least one of the images generated by the camera displays the probe; and a monitor receiving and responsive to signals from the camera for displaying the images generated by the camera.

19. The system of claim 18 further comprising a video recorder for recording the images generated by the camera.

20. The system of claim 18 wherein the monitor comprises a computer having a display, said computer receiving the images generated by the camera and displaying the images on its display.

21. The system of claim 20 further comprising an image processor for acquiring an image of the interior surface of the borehole from the images generated by the camera and for processing the acquired image.

22. The system of claim 21 wherein the images generated by the camera each include a plurality of pixels, said pixels each having a value representative of an optical characteristic of the images, and wherein the image processor processes the acquired image of the interior surface of the borehole as a function of the pixel values.

23. The system of claim 18 further comprising a rechargeable power supply for supplying power to the camera and/or the monitor.

24. The system of claim 18 further comprising a viewing envelope positioned adjacent the camera, said viewing envelope defining a viewing area adjacent the camera, and wherein the light source illuminates the viewing area.

25. The system of claim 24 wherein the viewing envelope comprises a transparent shell defining a fluid chamber.

26. The system of claim 25 wherein the fluid chamber of the viewing envelope is filled with water.

27. The system of claim 25 wherein the transparent shell comprises a rigid plastic.

28. The system of claim 25 wherein the transparent shell comprises a flexible plastic.

29. The system of claim 18 further comprising a motion control mechanism connected to the portable camera for controlling a viewing angle of the portable camera relative to an axis of the housing and comprising a rotational motion stage for tilting the viewing angle in a plane relative to the axis of the housing.

30. The system of claim 18 further comprising a motion control mechanism connected to the portable camera for controlling a viewing angle of the portable camera relative to an axis of the housing and comprising a rotational motion stage for rotating the viewing angle about the axis of the housing.

31. A system for visually inspecting an interior surface of a construction borehole, said system comprising:

a portable camera for generating images of a portion of the interior surface of the borehole and for generating signals representative of the generated images, said camera defining a viewing area adjacent the camera in which the images are generated;

a light source for illuminating at least a portion of the viewing area adjacent the camera thereby enabling the images of the interior surface of the borehole to be generated by the camera;

a housing for the camera and the light source, said housing adapted to be lowered into the borehole;

a probe for use with the housing for measuring a penetration of the probe on a bottom of the borehole and determining an amount of a deposit at the bottom of the borehole and wherein at least one of the images generated by the camera displays the probe, and wherein the probe comprises a graduated bar protruding from the housing and connected to the housing by a spring, said graduated bar being in the viewing area of the camera.; and a monitor receiving and responsive to signals from the camera for displaying the images generated by the camera.

* * * * *